US011592689B2

(12) United States Patent
Taylor et al.

(10) Patent No.: US 11,592,689 B2
(45) Date of Patent: Feb. 28, 2023

(54) ADAPTOR SYSTEM FOR EYEWEAR AND COCHLEAR IMPLANTS

(71) Applicant: Ferris State University, Big Rapids, MI (US)

(72) Inventors: Daniel A. Taylor, Big Rapids, MI (US); Jaclyn D. Vander Ploeg, Hudsonville, MI (US)

(73) Assignee: FERRIS STATE UNIVERSITY, Big Rapids, MI (US)

( * ) Notice: Subject to any disclaimer, the term of this patent is extended or adjusted under 35 U.S.C. 154(b) by 267 days.

(21) Appl. No.: 16/864,359

(22) Filed: May 1, 2020

(65) Prior Publication Data

US 2021/0341761 A1 Nov. 4, 2021

(51) Int. Cl.
| | |
|---|---|
| *H04R 25/02* | (2006.01) |
| *G02C 11/06* | (2006.01) |
| *H04R 25/00* | (2006.01) |
| *G02C 5/22* | (2006.01) |

(52) U.S. Cl.
CPC ............... *G02C 11/06* (2013.01); *G02C 5/22* (2013.01); *H04R 25/606* (2013.01); *H04R 25/607* (2019.05)

(58) Field of Classification Search
CPC ...... H04R 1/105; H04R 25/02; H04R 25/067; H04R 2225/021; H04R 2225/0213; H04R 2225/0216
See application file for complete search history.

(56) References Cited

U.S. PATENT DOCUMENTS

| | | | | |
|---|---|---|---|---|
| 2,882,348 A | * | 4/1959 | Erickson | H04R 25/602 |
| | | | | 381/322 |
| 5,694,475 A | * | 12/1997 | Boyden | H04R 1/1066 |
| | | | | 381/370 |
| 5,737,436 A | | 4/1998 | Boyden | |
| 6,748,094 B1 | * | 6/2004 | Tziviskos | H04R 25/607 |
| | | | | 381/322 |
| 7,142,926 B2 | * | 11/2006 | Crawford | H04R 25/606 |
| | | | | 607/57 |

(Continued)

FOREIGN PATENT DOCUMENTS

| | | | |
|---|---|---|---|
| EP | 1847868 | | 10/2007 |
| GB | 792742 A | * | 4/1958 |
| KR | 102195014 B1 | * | 12/2020 |

*Primary Examiner* — Ryan Robinson
(74) *Attorney, Agent, or Firm* — Warner Norcross + Judd LLP

(57) ABSTRACT

An adaptor system to facilitate use of eyewear with an audio processor for a cochlear hearing implant. The system includes an audio processor adaptor configured to mount to the audio processor and an eyewear adaptor configured to mount to the eyewear. The audio processor adaptor and the eyewear adaptor can be selectively connected to join the eyewear and the audio processor. The audio processor adaptor may include an ear hook portion that allows the audio processor to be worn over a wearer's ear even when separated from the eyewear. The adaptor system may be provided as a kit including a plurality of audio processor adaptors configured to mount to different audio processors and/or a plurality of eyewear adaptors configured to mount to different eyewear. The adaptors may include universal connectors that allow any audio processor adaptor to be interconnected with any eyewear adaptor.

16 Claims, 9 Drawing Sheets

(56) References Cited

U.S. PATENT DOCUMENTS

| | | |
|---|---|---|
| 7,735,996 B2 | 6/2010 | van der Zwan et al. |
| 8,098,865 B2 * | 1/2012 | Ho .................. H04R 25/607 |
| | | 381/330 |
| 8,233,651 B1 * | 7/2012 | Haller .............. H04R 25/456 |
| | | 381/328 |
| 9,380,374 B2 * | 6/2016 | Sprague ............ H04R 25/65 |
| 9,619,201 B2 * | 4/2017 | Jannard ............ H04R 1/1066 |
| 9,968,781 B2 * | 5/2018 | Roehrlein ......... H04R 25/554 |
| 2011/0234972 A1 | 9/2011 | LeBlang |
| 2017/0102560 A1 | 4/2017 | Murphy |
| 2021/0112346 A1 * | 4/2021 | Hilvers ............. H04R 25/556 |

* cited by examiner

ADAPTOR SYSTEM FOR EYEWEAR AND COCHLEAR IMPLANTS

BACKGROUND OF THE INVENTION

The present invention relates to cochlear implants, and more specifically, to accessories intended to facilitate the use of cochlear implants with eyewear.

Cochlear implants are devices that help users who have significant hearing loss. Unlike hearing-aids, which amplify sound, cochlear implants stimulate the cochlea with electrical impulses to mimic sound. The user undergoes surgery that installs the implant under the skin. A conductor link bridges the gap between the implant and the electrode contacts. The electrode contacts are inserted into the cochlea and stimulate the area. The electric impulses created by these electrodes allow the user to hear sound.

A conventional cochlear implant-based hearing system includes a number of components located outside the body to collect sound and wirelessly send corresponding signals from outside the body to the cochlear implant disposed under the skin. For example, a conventional cochlear-implant hearing system includes an audio processor and a coil. The audio processor includes a microphone that captures sound data and a processor that processes captured sound to create electrical signals corresponding to the sound. The electrical signals representing the captured sound are conveyed to the coil by a cable. The coil is disposed on the outside of the skin adjacent to the cochlear implant. As the electrical signals pass through the coil, the coil generates an electromagnetic field representative of the electrical signals. The electromagnetic field radiates wirelessly through the skin to the cochlear implant where the electromagnetic field is stimulates electric signals representative of the sound captured by the audio processor.

In many conventional systems, the audio processor is located on the user's ear and is kept in place by a hook that wraps around the front of the ear. This is an ideal location for many users as the ear is well-suited for supporting the audio processor. It also allows the user to put on and remove the audio processor with limited effort. Unfortunately, when the user wears glasses or other eyewear, the audio processor competes with the temple for the same space. As a result of the interference between these components, pain, swelling, irritation, rashes, and various other ailments can occur.

For some individuals, the solution is to use an audio processor that does not mount to the ear. A number of cochlear implant hearing systems have an "off-the-ear" audio processor that mounts at a location other than the ear. Some off-the-ear processors mount to the user's head, for example, by a magnet. Although this type of processor does not interfere with eyewear, it can interfere with hats, headbands and other headwear. Other off-the-ear processors have more diverse mounting options. For example, some conventional systems allow the audio processor to be mounted essentially anywhere on the wearer's body. While this gives more mounting options, a connecting cable extends between the processor and the coil and the cable capable must be long enough to accommodate the desired mounting position. The longer the cable, the more risk it can catch on things and otherwise be inconvenience to the user. Off-the-ear processors not only have their own unique disadvantages, but they are also extremely expensive, and are priced out of reach for many without sufficient insurance. As a result, some users have implemented a home fix that eliminates interference between eyewear and audio processors. These users cut the temple of the eyewear short enough so that the temple and the audio processor do not overlap. Although this avoids interference, it can make the eyewear uncomfortable and unstable.

As a result, there remain a long-felt and unmet need for an accessory capable of effectively and inexpensively joining the audio processor for a cochlear implant with an item of eyewear.

SUMMARY OF THE INVENTION

The present invention provides an adaptor system that allows cochlear audio processors to be coupled to an item of eyewear, such as prescription or non-prescription glasses. The adaptor system includes multiple parts with a first adaptor configured to mount to the audio processor (audio processor adaptor) and a second adaptor configured to mount to the eyewear (eyewear adaptor). The two adaptors are configured to be selectively interconnected so that the audio processor and the eyewear can be joined and separated as desired.

In one embodiment, the adaptor system is configured for use with cochlear audio processors that include a removable ear hook. In this embodiment, the audio processor adaptor is configured to mount to the audio processor in place of the stock removable ear hook. In this context, the audio processor adaptor may have a portion that is in the form of an ear hook. For example, the audio processor adaptor may have an ear hook portion designed to extend around a portion of the ear to hold the audio processor in place on the ear. In one embodiment, the ear hook portion mimics the form of the removable ear hook provided stock with the audio processor.

The audio processor adaptor may be secured to the audio processor using any suitable attachment. When used with audio processors that have a removable ear hook, the audio processor adaptor may be attached to the audio processor using the pre-existing attachment structure intended for use with the removable ear hook. For example, when configured for use with audio processors that have a removable ear hook held in place by friction, the audio processor adaptor may be configured to attach to the audio processor by friction. In some implementations of this type, the audio processor adaptor may have an attachment portion that mirrors the attachment portion of the stock removable ear hook. In other applications, the audio processor adaptor may be secured to the audio processor using other attachments or combinations of attachments, such as fasteners, adhesive, snap rings, pins, catches, shrink tubes and other similar structures.

In one embodiment, the eyewear adaptor is configured to mount to one of the pre-existing temples of the eyewear. In this embodiment, the eyewear adaptor is configured to be mounted directly to a temple after the temple has been modified to receive the eyewear adaptor. For example, the temple may be cut to remove the portion of the temple that would otherwise occupy space consumed by the audio processor adaptor and the audio processor. In typical applications, this includes removing the portion of temple that would extend over and behind the ear. The appropriate portion of the temple, including the temple tip, may be removed by cutting the temple. In some cases, attachment of the eyewear adaptor, including cutting of the temple, may be done by an optician. Alternatively, the temple could be cut and/or the eyewear adaptor could be installed at home by the end user.

In one embodiment, the eyewear adaptor is configured to be frictionally fitted to the temple without the need for adhesive, fasteners or other supplemental attachment materials or components. In one embodiment, the eyewear adaptor includes a temple seat defining a space configured to receive the end portion of the temple and a temple connector situated at the entry to the temple seat for gripping or otherwise securing the temple. In one embodiment, the temple connector is configured to frictionally hold to the temple. For example, the temple connector may include a plurality of fingers that define a slot or other aperture capable of accepting and firmly holding the temple. In this context, the aperture is narrower than the temple so that one or more of the fingers are required to deflect to receive the temple as the temple is pushed through the temple connector into the temple seat. The deflection continues while the temple remains in the temple connector so that the fingers apply a continuous retention force to the temple. The aperture and fingers are designed so that it is not too difficult to insert the temple through the temple connector into the temple seat, while at the same time providing sufficient retention force to retain the temple and resist its inadvertent removal from the temple seat during day-to-day use.

In alternative applications, the eyewear adaptor may connect to the eyewear using alternative types of connections. In some applications, the eyewear adaptor may be secured to the temple by epoxy or adhesives. For example, the temple may be secured in a temple seat by epoxy or adhesives. In other applications, the eyewear adaptor may be capable of clamping or otherwise closing onto the temple to provide a more secure interconnection. For example, the eyewear adaptor may include two parts that can be clamped together about the temple to secure the adaptor to the temple. In another example, the temple connector may be capable of insertion into the temple seat and the two components may be configured to interact so that the temple connector closes more as the temple connector is move farther into the seat. For example, the temple connector may be a collet that is threaded into the temple seat and increasingly closes onto the temple as it is threaded farther into the temple seat.

In one embodiment, the eyewear adaptor and the audio processor adaptor are configured to be readily joined and separated. As a result, the eyewear and audio processor can be used together or they can be separated and used apart from one another. For example, the user may remove the audio processor from the eyewear so that the audio processor can be used even when it is not desirable to wear eyewear. The use of an audio processor adaptor with an ear hook portion facilitates this option. It also allows the consumer to use the eyewear separate from the audio processor.

In some applications, the adaptor assembly may include a replacement temple tip that can be removably attached to the eyewear adaptor in place of the audio processor. The replacement temple tip may be designed to extend the temple and to hook or curl around the ear in much the same manner as the portion of the temple that was removed to allow installation of the eyewear adaptor. In implementations of this type, the replacement temple tip may include a universal connector that allows the replacement temple tip to attach to the universal connector on the eyewear adaptor in place of the audio processor adaptor. In some applications, the adaptor system is provided with a plurality of different replacement temple tips of different sizes, shapes and styles.

In one embodiment, the adaptor system may be provided as a kit with a plurality of alternative eyewear adaptors and/or a plurality of alternative audio processor adaptors that can be interchangeably used to join a wide range of cochlear audio processors to a wide range of eyewear. The eyewear adaptors and audio processor adaptors can be provided with universal fittings that allow any eyewear adaptor to be connected to any audio processor adaptor, thereby allowing any audio processor to be easily attached to any eyewear. Conventional audio processors come in different shape and styles. For example, the kit may include a variety of different audio processor adaptors with each one having a different audio processor interface for attachment to a different type of audio processor. Similarly, each eyewear adaptor may be configured to attach to a particular size, type or style of temple or range of sizes, types or styles of temples. In some applications, the adaptor assembly kit may be provided with a variety of alternative replacement temple tips of different sizes, shapes and styles.

The present invention provides a simple and effective adaptor system that allows an audio processor for a cochlear implant to be secured to an item of eyewear. In some embodiments, the adaptor system can be easily mounted to an audio processor in the place of a stock removable ear hook. This makes it particularly easy for the adaptor system to be used with cochlear implants that have removable ear hooks. It also allows the adaptor system to be easily removed from the audio processor and for the stock ear hook to be returned. The use of a multipart adaptor system with separate audio processor adaptors and eyewear adaptors with universal connectors allows a range of different audio processors to be attached to a range of different items of eyewear. The system can be configured to work with new audio processors and new eyewear by introducing new audio processor adaptors and/or new eyewear adaptors. In applications in which the audio processor adaptor includes an ear hook portion, the audio processor adaptor is capable of holding the audio processor on the ear even the audio processor adaptor is not attached to the eyewear. In applications that include a replacement temple tip, the eyewear can be comfortably and stably worn even when separated from the audio processor.

These and other features of the invention will be more fully understood and appreciated by reference to the description of the embodiments and the drawings.

Figure 1:
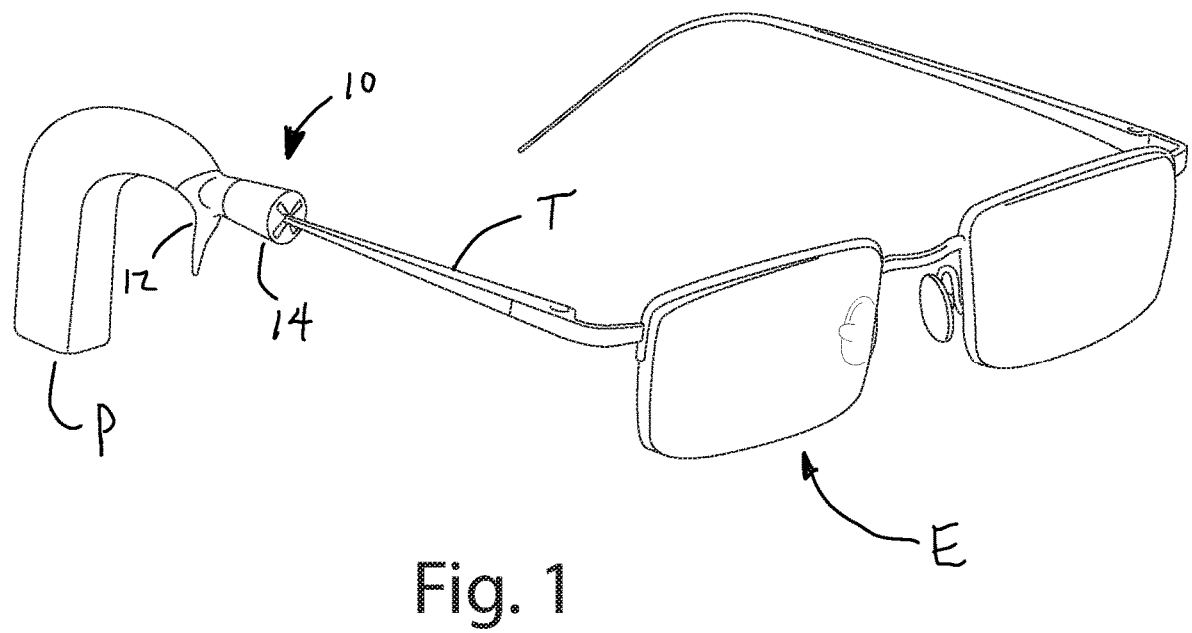
FIG. 1 is a perspective view of an audio processor for a cochlear hearing implant mounted to a pair of glasses using an adaptor system in accordance with an embodiment of the present invention.

Before the embodiments of the invention are explained in detail, it is to be understood that the invention is not limited to the details of operation or to the details of construction and the arrangement of the components set forth in the following description or illustrated in the drawings. The invention may be implemented in various other embodiments and of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the invention to any specific order or number of components. Nor should the use of enumeration be construed as excluding from the scope of the invention any additional steps or components that might be combined with or into the enumerated steps or components.

DESCRIPTION OF CURRENT EMBODIMENTS

A. Overview.

An item of eyewear connected with an audio processor for a cochlear hearing implant using an adaptor system 10 in accordance with an embodiment of the present invention is shown in FIG. 1. The adaptor system 10 includes multiple parts with an audio processor adaptor 12 configured to mount to the audio processor P and an eyewear adaptor 14 configured to mount to the eyewear E. The audio processor adaptor 12 and the eyewear adaptor 14 are configured to be removably joined to one another to allow the audio processor P to be selectively coupled to the item of eyewear E, and thereby facilitate simultaneous use of eyewear and a cochlear hearing implant. The audio processor adaptor 12 may include an ear hook portion that allows the audio processor P to be fitted to a wearer's ear even when the eyewear is not connected to the audio processor P. This facilitates use of the audio processor P without the eyewear E, when desired. The adaptor system 10 may be provided as a kit including one or more audio processor adaptors 12 configured to mount to different audio processors P and a plurality of eyewear adaptors 14 configured to mount to different items of eyewear E. The audio processor adaptors 12 and eyewear adaptors 14 are interchangeable and are provided with universal connectors so that any audio processor adaptor 12 can be joined to any eyewear adaptor 14, thereby allowing essentially any audio processor P to be connected to essentially any eyewear E. In some applications, the adaptor system 10 may also include one or more replacement temple tips 16 that can be removably attached to the eyewear adaptor 14 in place of the audio processor adaptor 12. The replacement temple tips 16 facilitate use of the eyewear E without the audio processor P attached, when desired.

B. Detailed Description.

As noted above, the present invention provides an adaptor system 10 that allows an audio processor P for a cochlear implant to be coupled to an item of eyewear E, such as prescription or non-prescription glasses. The present invention is illustrated in connection with an adaptor system 10 connected to the right temple of an item of eyewear. The adaptor system 10 may be used to couple an audio processor P to either or both temples T. The adaptor system 10 generally includes an audio processor adaptor 12 configured to mount to the audio processor and an eyewear adaptor 14 configured to mount to the eyewear. The two adaptors 12 and 14 are configured to be selectively joined together to couple the audio processor P to the eyewear E. Audio processors P are available in a variety of different types and designs and the adaptor system 10 may include a plurality of audio processor adaptors 12, each designed to fit a different type or design of audio processor P (or range of audio processors P). Similarly, eyewear is available in a variety of different types and designs, and the adaptor system 10 may be include a plurality of eyewear adaptors 14, each designed to fit a different type or design of eyewear E (or range of different eyewear E).

The audio processor adaptor 12 may be configured to mount to the audio processor P using any suitable mounting structure. When designed for use with audio processors that have a removable ear hook, the audio processor adaptor 12 may be configured to mount to the audio processor P in place of the removable ear hook, and may attach using the pre-existing attachment structure intended for use with the removable ear hook (not shown). For example, when configured for use with an audio processor having a removable ear hook held in place by a friction fit, the audio processor adaptor 12 may have a connector end that mirrors the connector end of the removable ear hook and it therefor capable of being friction fit to the audio processor in place of the stock ear hook. When intended for use with audio processors that do not have a removable ear hook or a pre-existing ear hook mounting structure capable of coupling to the audio processor adaptor 12, the audio processor adaptor 12 may be configured to mount to the audio processor using other types of connections, such as adhesive (temporary or permanent), fasteners, snap rings, pins, catches, shrink tubes and/or a form of mechanical interlock between the audio processor adaptor and the audio processor housing.

Figure 2:
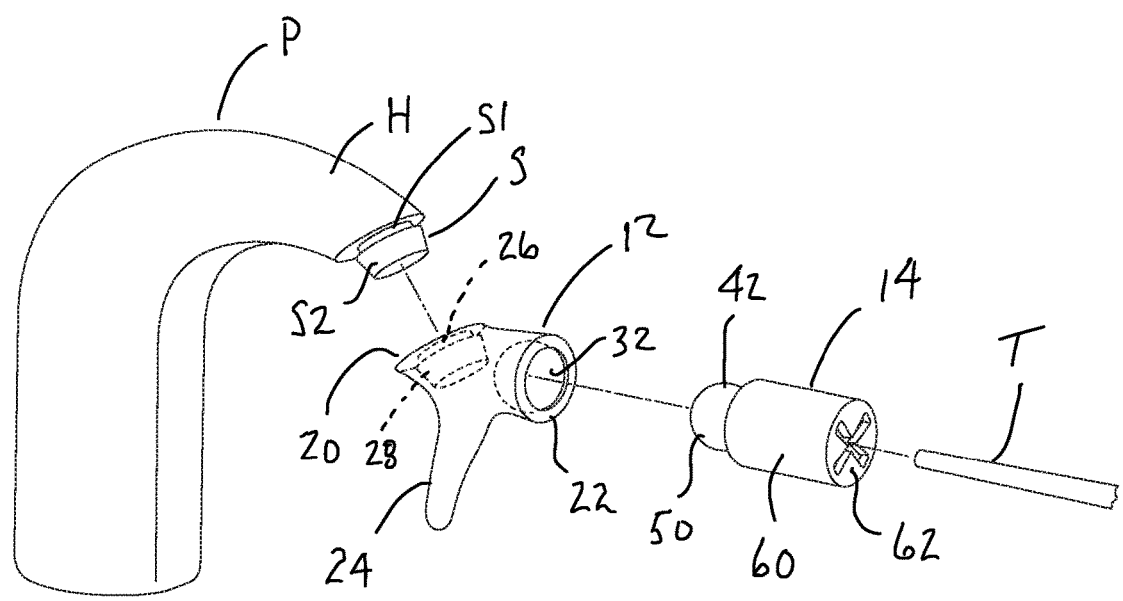
FIG. 2 is an exploded view of an audio processor for a cochlear hearing implant, glasses and adaptor system.
Figure 6:
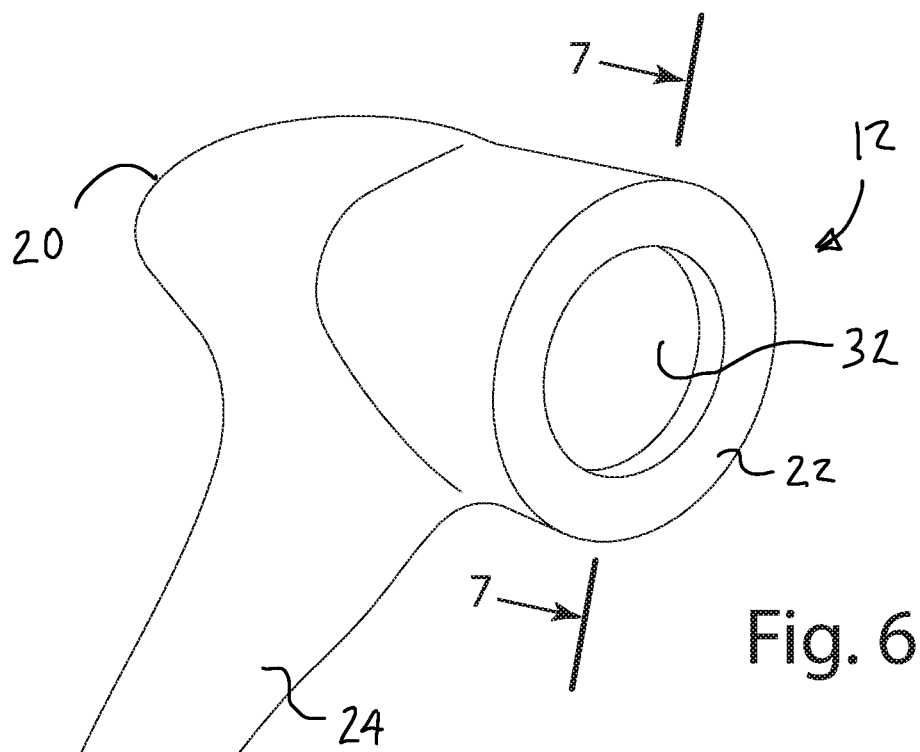
FIG. 6 is a perspective view of the audio processor adaptor.
Figure 7:
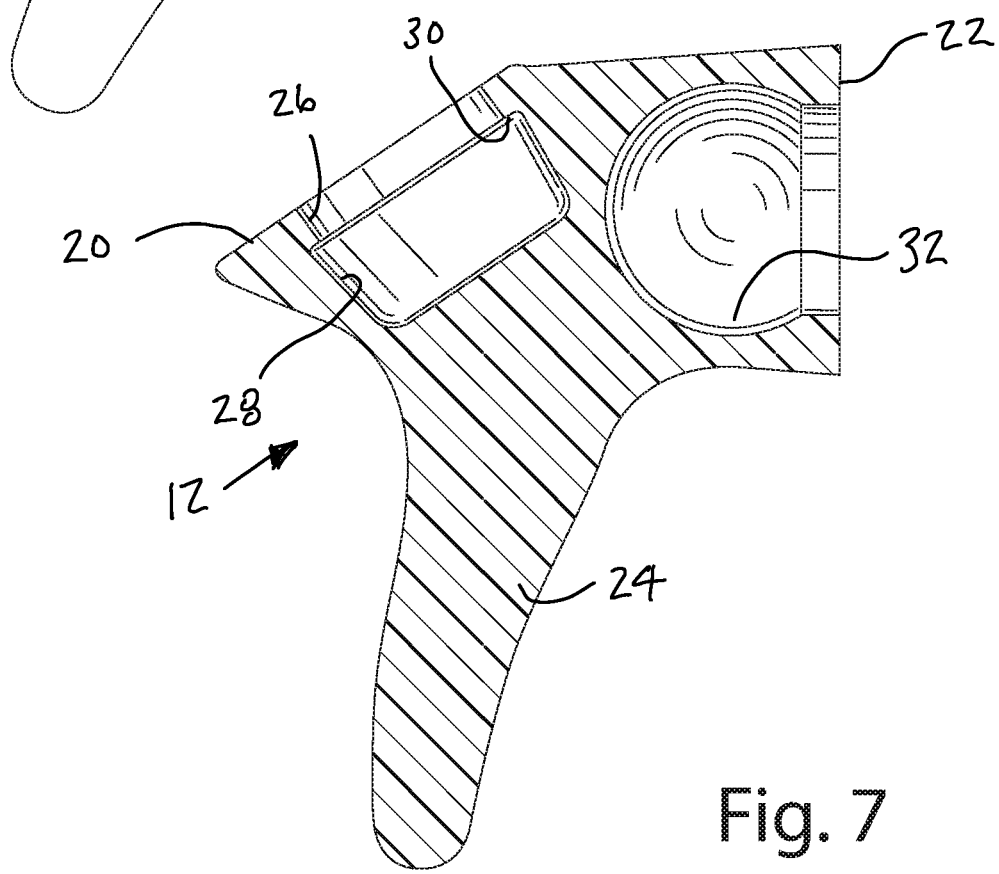
FIG. 7 is a sectional view of the audio processor adaptor.

Referring now to FIGS. 1 and 2, the adaptor system 10 of the illustrated embodiment is configured for use with cochlear audio processors P that include a removable ear hook (not shown). In this embodiment, the audio processor adaptor 12 is configured to mount to the audio processor P in place of the stock removable ear hook. As shown in FIGS. 6 and 7, the audio processor adaptor 14 is a one-piece component that generally includes an attachment end 20 configured to attach to the audio processor P, a connector end 22 configured to removably connect to the eyewear adaptor 14 and an ear hook portion 24 configured to engage a wearer's ear. As noted above, the attachment end 20 of the illustrated embodiment is configured to connect to a pre-existing mounting structure on the audio processor P. For example, the audio processor P shown in the illustrations includes a pre-existing mounting stub S that protrudes from the housing H to receive and support the stock ear hook (not shown). By taking advantage of the pre-existing mounting stub S, no modifications to the audio processor P are required to install the audio processor adaptor 12 on the audio processor. Instead, the attachment end 20 of the audio processor adaptor 12 can be simply be pushed onto the mounting stub S in place of the stock ear hook. As perhaps best shown in FIG. 2, the pre-existing mounting stub S is a cylindrical or tubular structure 51 that extends from the housing H and terminates at its outer end in an enlarged lip or barb S2. To interfit with the mounting stub S, the attachment end 20 defines a cylindrical opening 26 with an enlarged internal head 28. The cylindrical opening 26 corresponding in diameter with the tubular structure 51 and the head 28 corresponds in diameter with the barb S2 so that the barb S2 becomes entrapped in head 28 when the mounting stub S is fully inserted into the audio processor adaptor 12. The radial surface 30 of the head 28 may be configured to help control the amount of force required to remove the audio processor adaptor 12 from the mounting stub S. For example, the surface 30 may be inwardly inclined toward the cylindrical opening 26 to facilitate removal by providing a ramp-like surface that aids transition of the barb S2 from the head 28 into the cylindrical opening 26. Alternatively, the force required to remove the audio processor adaptor 12 can be increased by, for example, orienting the radial surface 30 perpendicular to the axis of the cylindrical opening 26, thereby eliminating any assistance that surface might otherwise provide in removing the barb S2 from the head 28. In the illustrated embodiment, the audio processor adaptor 12 is manufactured from a material this is sufficiently pliable and resilient to allow the desired interconnection with the audio processor P. The connecting structure provided in the attachment end 20 is designed for use with the illustrated audio processor P and other audio processors with sufficiently similar mounting structures. With audio processors that have different mounting structure, the design and configuration of the attachment end 20 of the audio processor adaptor 12 may be varied to correspond with the pre-existing mounting structure of the desired audio processor.

The connector end 22 of the audio processor adaptor 12 is configured to removably connect with the eyewear adaptor 14 to allow the audio processor P to be selectively coupled to the eyewear E. In the illustrated embodiment, the connector end 22 of the audio processor adaptor 12 is configured to mount to a corresponding connector end 42 of the eyewear adaptor 12, which is discussed in more detail below. The two connector ends 22 and 42 may have essentially any type of connection that allows the eyewear adaptor 14 and the audio adaptor 12 to be selectively connected and separated. In the illustrated embodiment, the two connector ends 22 and 42 include a ball and cup attachment. More specifically, the connector end 22 of the audio processor adaptor 12 defines a cup 32 and the connector end of 42 of the eyewear adaptor 14 includes a ball 50 configured to be fitted tightly within the cup 32. When the connector ends 22 are coupled, the fit may be set to allow the adaptors 12 and 14 to twist about the connection to or it may be set to prevent twisting in applications where it is desirable to affixed the audio processor P at a fixed angle.

Figure 14:
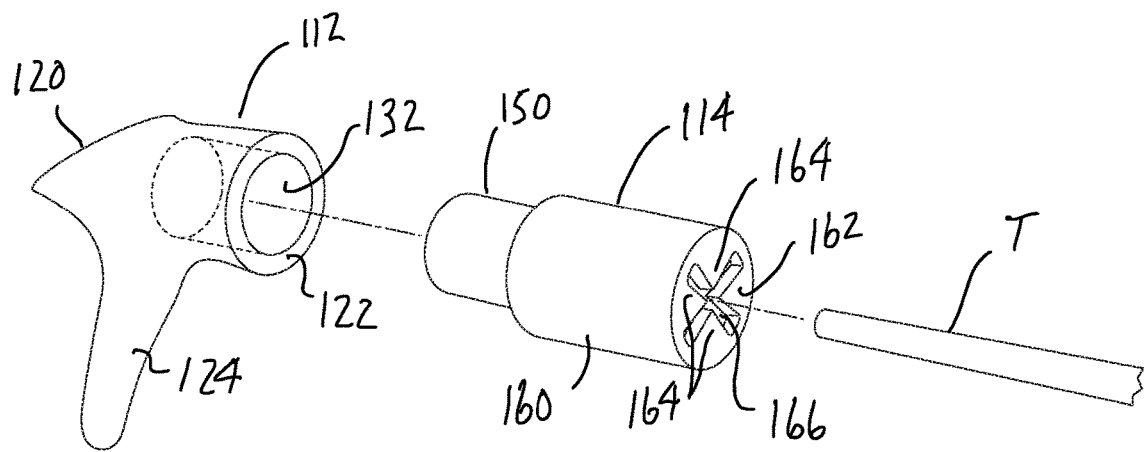
FIG. 14 is a perspective, exploded view of an eyewear adaptor and audio processor adaptor with alternative universal connectors.
Figure 15:
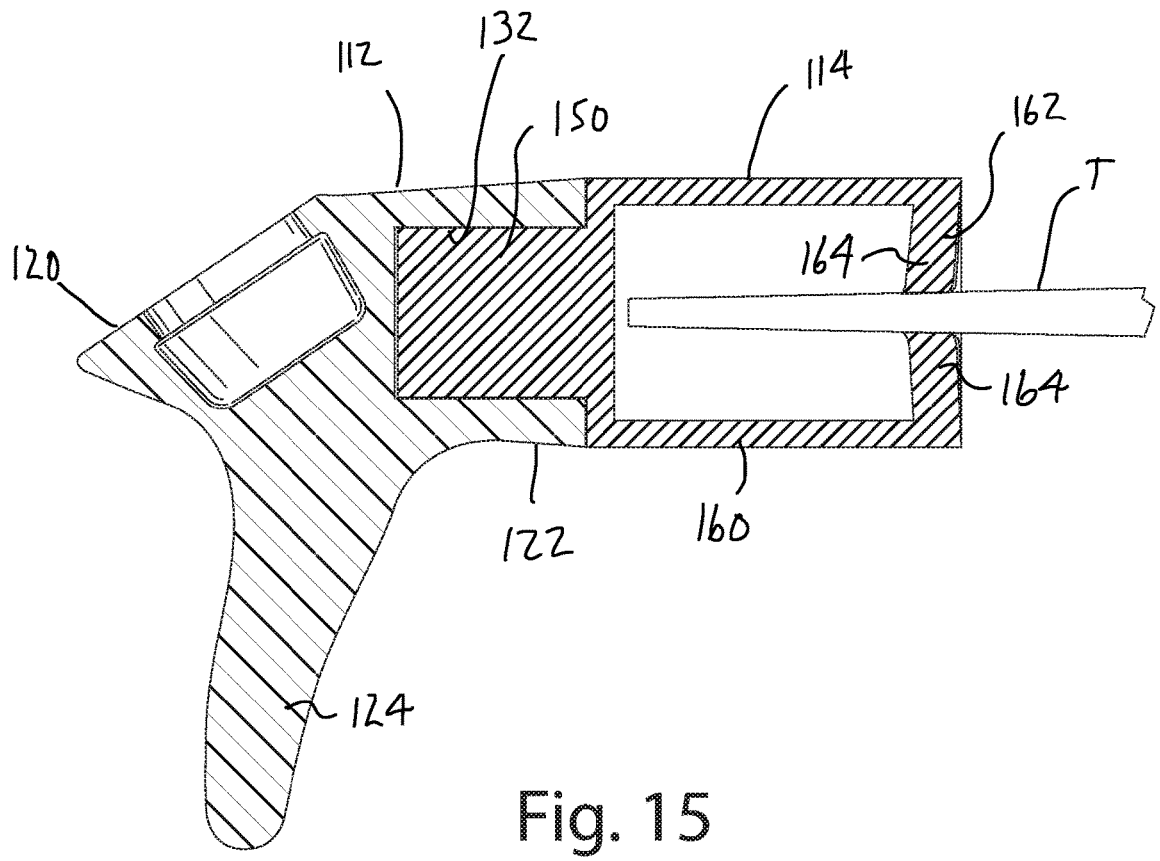
FIG. 15 is a sectional view of the eyewear adaptor and audio processor adaptor with alternative universal connectors.

In alternative embodiments, the connector ends 22 and 42 may include different types of connections. This may include different snap-together or friction-fit connections. For example, FIGS. 14 and 15 show an alternative adaptor system 110 with a different type of connection. FIGS. 14 and 15 incorporate reference numerals that correspond with those used in connection with adaptor system 10, except that they are preceded with a "1" in the hundreds place (e.g. adaptor system 110 is analogous to adaptor system 10, audio processor adaptor 112 is analogous audio processor adaptor 12 and eyewear adaptor 114 is analogous to eyewear adaptor 14). As shown, adaptor system 110 includes an audio processor adaptor 112 having a connector end 122 defining a cylindrical opening 132 and an eyewear adaptor 114 having a connector end with a cylindrical post 150. The cylindrical post 150 is configured to tightly fit within the cylindrical opening 132. Although not shown, the cylindrical post 150 may be provided with a head and the cylindrical opening 132 may be provided with a corresponding annular opening configured to receive the head to provide a snap-fit connection. Further, the cylindrical post 150 and the cylindrical opening 132 may be keyed to ensure a specific rotational alignment between the two adaptors 112 and 114. The connection could be implemented with a wide range of other types or styles of connections. For example, the connection between the adaptors could alternatively be a threaded connection with one connector end including male threads and the other connector end including female threads. As another example, the adaptors may include a bayonet-type connection with one connector end including lugs that fit into corresponding channels in the other connector end.

In some applications, it may be desirable to incorporate one or more magnets into the connection between the adaptors. For example, one connector end may include a magnet and the other connector end may include a magnet or a magnetically-attractable material. The magnet(s) may help supplement another type of connection and enhance the tactile response or may form the primary connection. The strength of the magnetic connection can be controlled, in part, through selection of the magnet(s) and/or the magnetically-attractable material.

As noted above, the ear hook portion 24 is configured to engage the wearer's ear. The size, shape and style of the ear hook portion 24 may vary from application to application, but is generally designed to extend around a portion of the ear to hold the audio processor P in place on the ear even when separated from the eyewear E. In the illustrated embodiment, the ear hook portion 24 generally mimics the form of the ear hook (not shown) provided stock with the audio processor P. However, the ear hook portion 24 need not mimic the form of the stock ear hook, but can be of essentially and desired size and shape.

Figure 8:
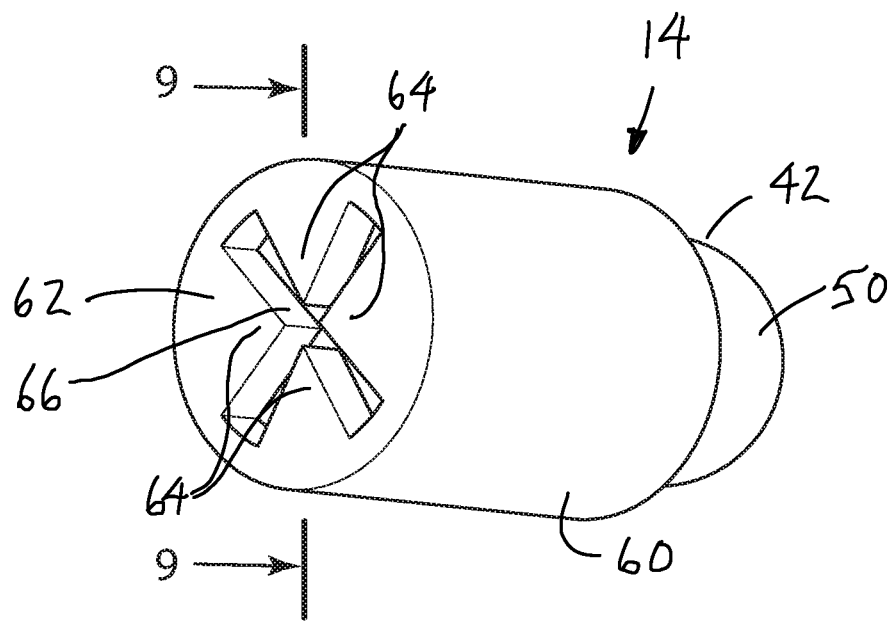
FIG. 8 is a perspective view of the first eyewear adaptor.
Figure 9:
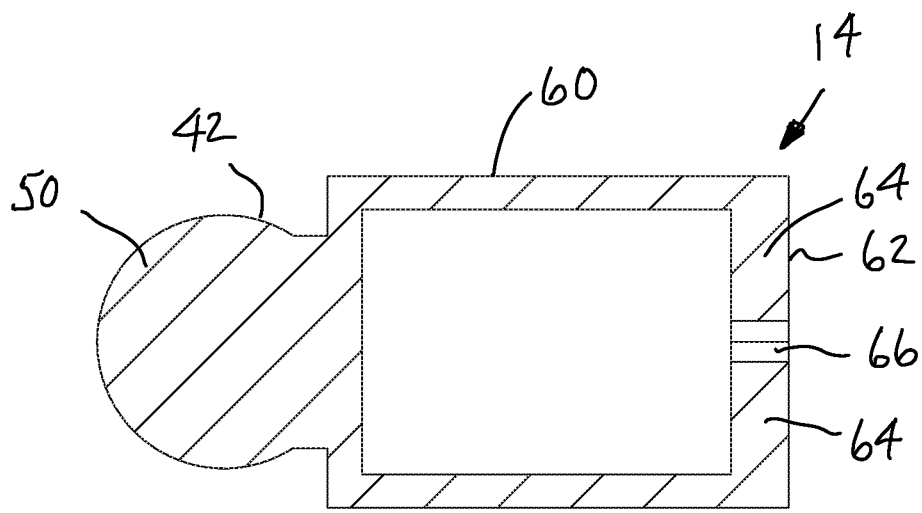
FIG. 9 is a sectional view of the first eyewear adaptor.

As noted above, the eyewear adaptor 14 is configured to mount to an item of eyewear E, and to provide a connection for selectively joining the eyewear adaptor 14 to the audio processor adaptor 12 (See FIGS. 8 and 9). In the illustrated embodiment, the eyewear adaptor 14 is configured to mount to one of the pre-existing temples T of the eyewear E. In this embodiment, the eyewear adaptor 14 is configured to be mounted directly to a temple T after the temple T has been modified to receive the eyewear adaptor 14. For example, the temple T may be cut to remove the portion of the temple T that would otherwise occupy space consumed by the audio processor adaptor 12 and the audio processor P. In typical applications, this includes removing the portion of temple T that would extend over and behind the ear. The appropriate portion of the temple T may be removed by cutting the temple T with any suitable cutting implement. In some cases, attachment of the eyewear adaptor 14, including cutting of the temple T, may be done by an optician. Alternatively, the temple T can be cut and/or the eyewear adaptor 14 can be installed at home by the end user.

Figure 3A:
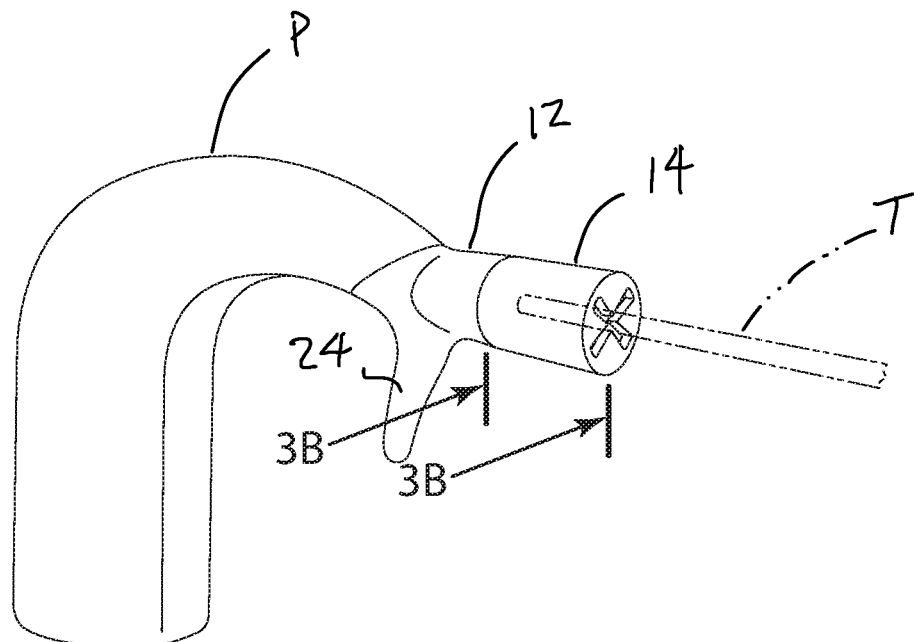
FIG. 3A is a perspective view of the adaptor system with a first eyewear adaptor mounted to an audio processor.
Figure 3B:
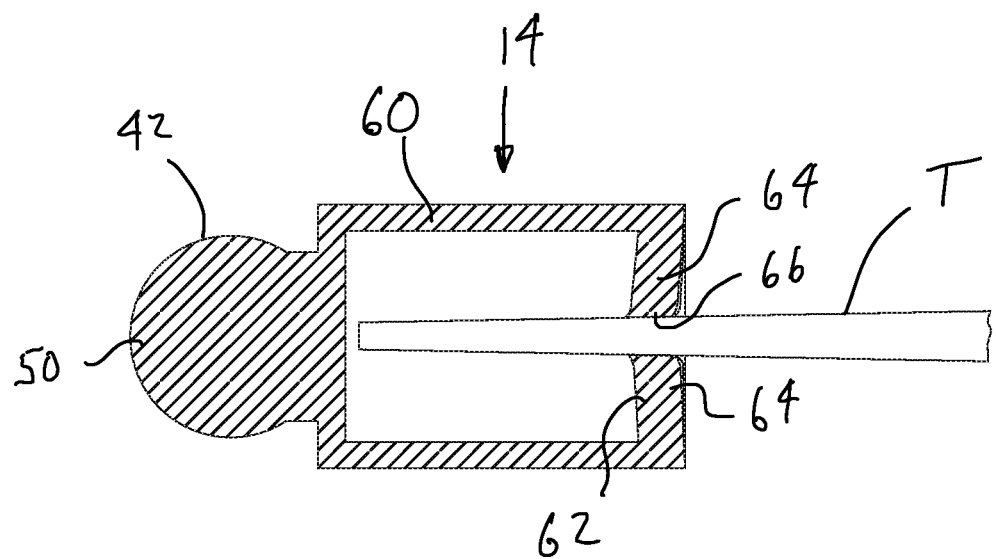
FIG. 3B is a sectional view similar to FIG. 3A showing the temple fitted within the first eyewear adaptor.
Figure 4:
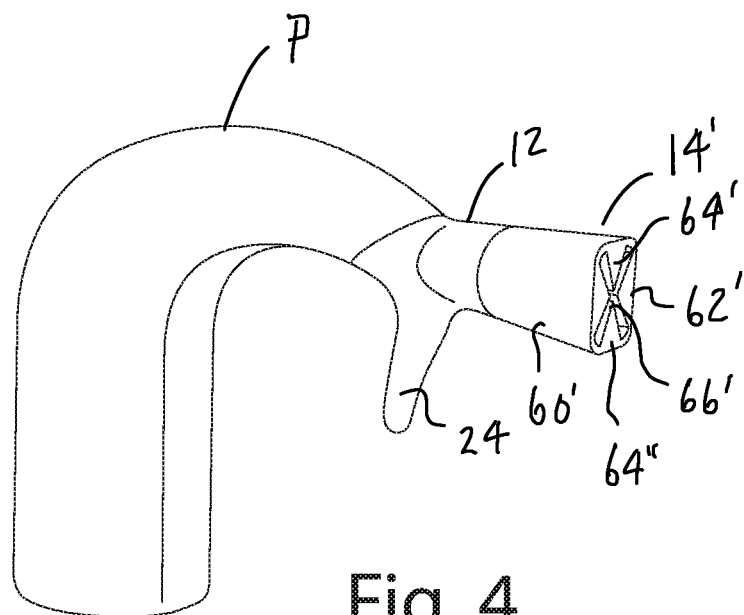
FIG. 4 is a perspective view of the adaptor system with a second eyewear adaptor mounted to an audio processor.
Figure 5:
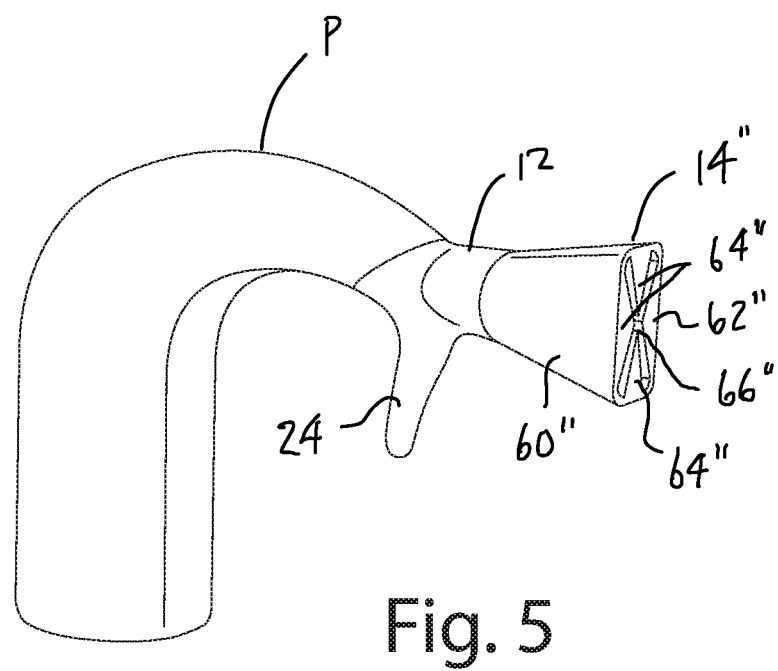
FIG. 5 is a perspective view of the adaptor system with a third eyewear adaptor mounted to an audio processor.

Referring now to FIGS. 3A and 3B, the illustrated eyewear adaptor 14 is configured to be frictionally fitted to the temple T without the need for adhesive, fasteners or other supplemental attachment materials or components. As shown, the eyewear adaptor 14 includes a temple seat 60 defining a space configured to receive the end portion of the temple T and a temple connector 62 situated at the entry to the temple seat 60 for gripping the temple T. In this embodiment, the temple connector 62 is configured to frictionally engage the end of the temple T. For example, the temple connector 62 may include a plurality of fingers 64 that define one or more slots 66 or other apertures capable of accepting and firmly holding the temple T. In the embodiment of FIG. 3B, the slot 66 is narrower than the temple T so that one or more of the fingers 64 are required to deflect to receive the temple T as the temple T is pushed through the slot 66 in the temple connector T into the temple seat 60. The deflection of the finger(s) 64 continues while the temple T remains in the temple connector 62 so that the finger(s) 64 apply a continuous retention force to the temple T. The slot 66 and fingers 64 are designed so that it is not too difficult to insert the temple T through the temple connector 62 into the temple seat 60, while at the same time providing sufficient retention force to retain the temple T and resist its inadvertent removal from the temple seat 60 during day-to-day use. For example, the size and shape of the slot 66 (or other aperture), the size and shape of the fingers 64 and the material properties of the fingers 64 may be selected to set the desired characteristics of the temple connector 62.

In alternative applications, the eyewear adaptor 14 may connect to the eyewear E using alternative types of connections. In some applications, the eyewear adaptor 14 may be secured to the temple T by epoxy or adhesive. For example, the temple T may be secured in the temple seat 60 by epoxy or adhesive. In the context of the illustrated embodiment, epoxy or adhesive may be introduced into the interior of the temple seat 60 in the space occupied by the temple T and allowed to cure to form an essentially permanent connection between the temple T and the temple seat 60. In still other applications, the eyewear adaptor 14 may be capable of clamping or otherwise closing onto the temple T to provide the desired interconnection. For example, an alternative eyewear adaptor (not shown) may include two parts that can be clamped together about the temple T to secure the adaptor to the temple. The parts may be clamped by fasteners or other suitable mechanisms capable of drawing the adaptor parts together with sufficient force. In yet another example, the temple connector 62 may be capable of insertion into the temple seat 60 and the two components may be configured to interact so that the temple connector 62 closes more as the temple connector 62 is move farther into the seat 60. For example, the temple connector 62 may be in the form of a tapered collet that is fitted into the temple seat 60 and increasingly closes onto the temple T as it is fitted farther into the temple seat 60. As with conventional collet arrangements, the temple connector 62 may be secured in the temple seat 60 by a threaded cap (not shown).

In the illustrated embodiment, the eyewear adaptor 14 and the audio processor adaptor 12 are configured to be easily and quickly joined and separated by user. This permits the eyewear E and audio processor P to be used together or to be separated and used apart from one another. For example, the user may remove the audio processor P from the eyewear E by separating the adaptors so that the audio processor P can be used even when it is not desirable to wear eyewear E. The use of an audio processor adaptor 12 with an ear hook portion 24 facilitates this option as the ear hook portion 24 can be used to retain the audio processor P on the ear. It also allows the consumer to use the eyewear E separate from the audio processor P.

Figure 16:
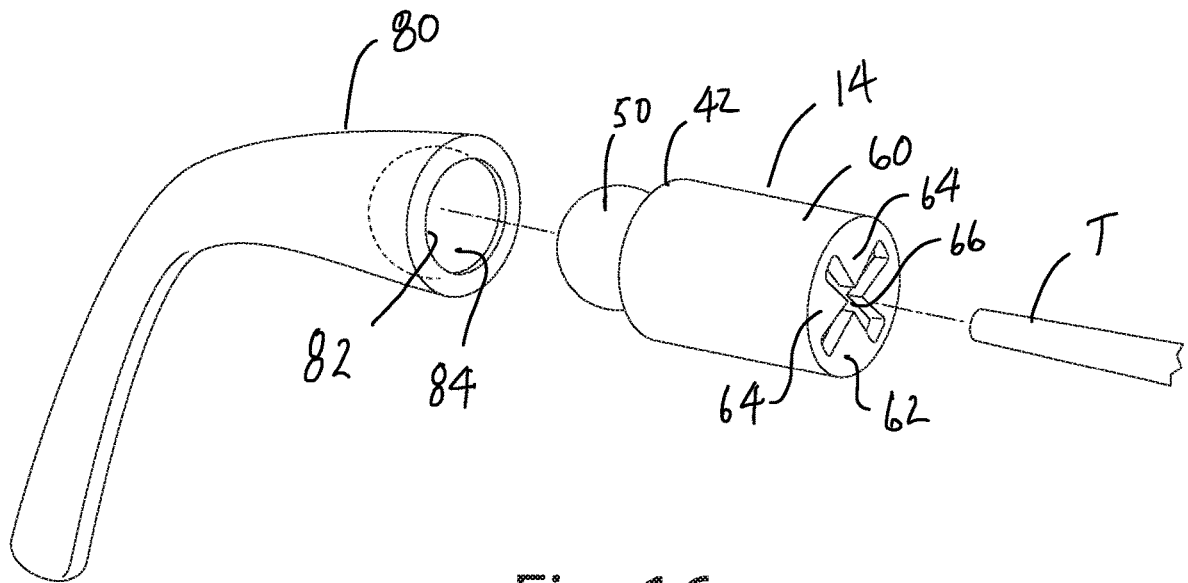
FIG. 16 is a perspective view of a first temple replacement.
Figure 17:
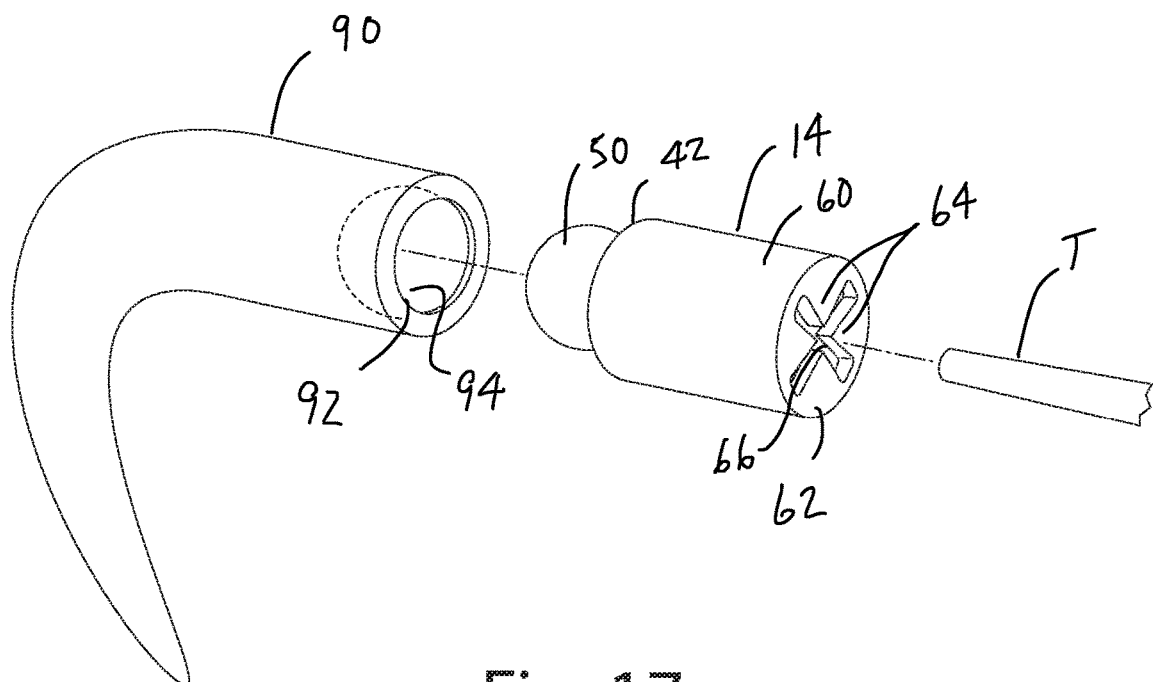
FIG. 17 is a perspective view of a second temple replacement.

In some applications, the adaptor system 10 may include a replacement temple tip 80 that can be removably attached to the eyewear adaptor 14 in place of the audio processor adaptor 12 and the audio processor P. A replacement temple tip 80 in accordance with an embodiment of the present invention is shown in FIG. 16. The replacement temple tip 80 is designed to extend the temple T and to curl around the ear in much the same manner as the portion of the temple that was removed to allow installation of the eyewear adaptor 14 to the temple T. In use, the replacement temple tip 80 may be attached to the eyewear adaptor 14 in place of the audio processor adaptor 12 when it is desirable to wear the eyewear without the audio processor P. The replacement temple tip 80 may be configured to attach to the eyewear adaptor 14 using essentially any suitable connection. However, in the illustrated embodiments, the replacement temple tip 80 is configured to connect to the eyewear adaptor 14 using the same attachment structure used to attach the audio processor adaptor 12. In implementations of this type, the replacement temple tip 80 may include a universal connector 82 that allows the replacement temple tip 80 to attach to the connector end 42 on the eyewear adaptor 14. As described above, the connector end 42 of the eyewear adaptor 14 includes a ball 50, and the replacement temple tip 80 defines a cup 84 adapted to firmly receive the ball 50. The design and configuration of the ball 50 and cup 84 are selected to provide a connection that is sufficient to hold the replacement temple tip 80 in place on the temple T until intentionally removed by the user. In applications where the adaptors 12 and 14 include an alternative connection structure, the replacement temple tip 80 can be adapted to interchangeably connect with the alternative connection structure. The replacement temple tip 80 of FIG. 16 is merely exemplary and may vary from application to application. For example, FIG. 17 shows an alternative replacement temple tip 90 with a different shape. The alternative replacement temple tip 90 includes a narrower temple structure that wraps around the ear and may be more suitable for using in athletics and other activities. The replacement temple tip 90 includes a universal connector, such as cup 94, so that it can be interchangeably attached to the eyewear adaptor 14. In some applications, the adaptor system 10 is provided with a plurality of replacement temple tips of different sizes, shapes, styles, materials and colors. Although the embodiments of FIGS. 16 and 17 are ambidextrous, specific left and right replacement temple tips may be provided, if desired. In some applications, the kit may include a replacement temple tip adaptor (not shown) that allows the portion of the temple cut from the eyewear E to be used as part of the replacement temple tip. For example, the replacement temple tip adaptor may be generally identical to the eyewear adaptor 14, except that it includes the opposite connector end, so that it can be removable attached to the eyewear adaptor.

Figure 10:
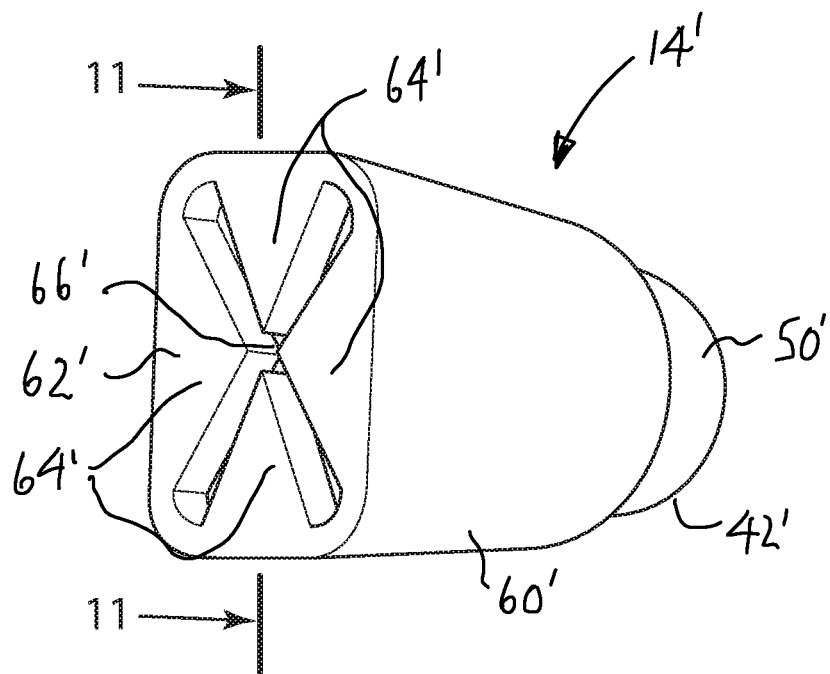
FIG. 10 is a perspective view of the second eyewear adaptor.
Figure 11:
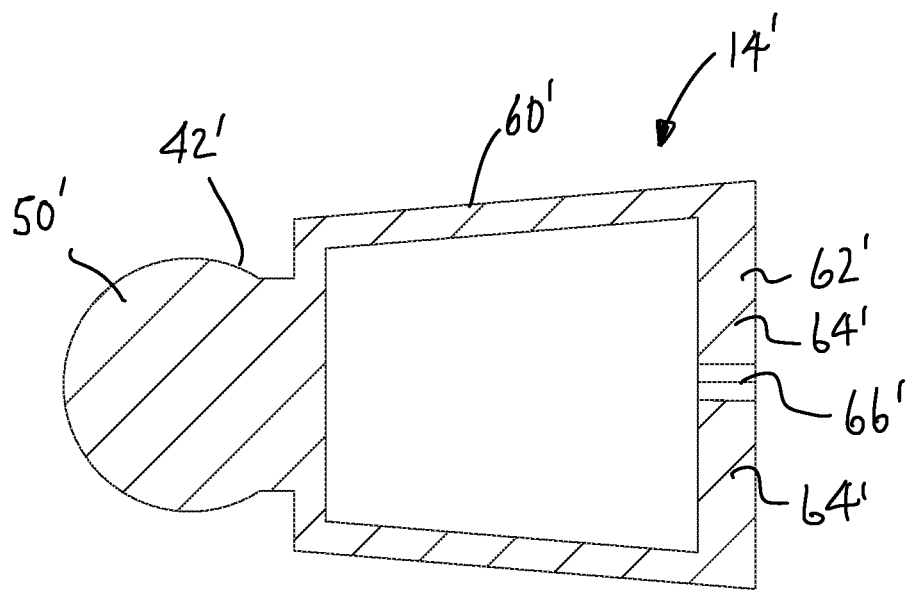
FIG. 11 is a sectional view of the second eyewear adaptor.
Figure 12:
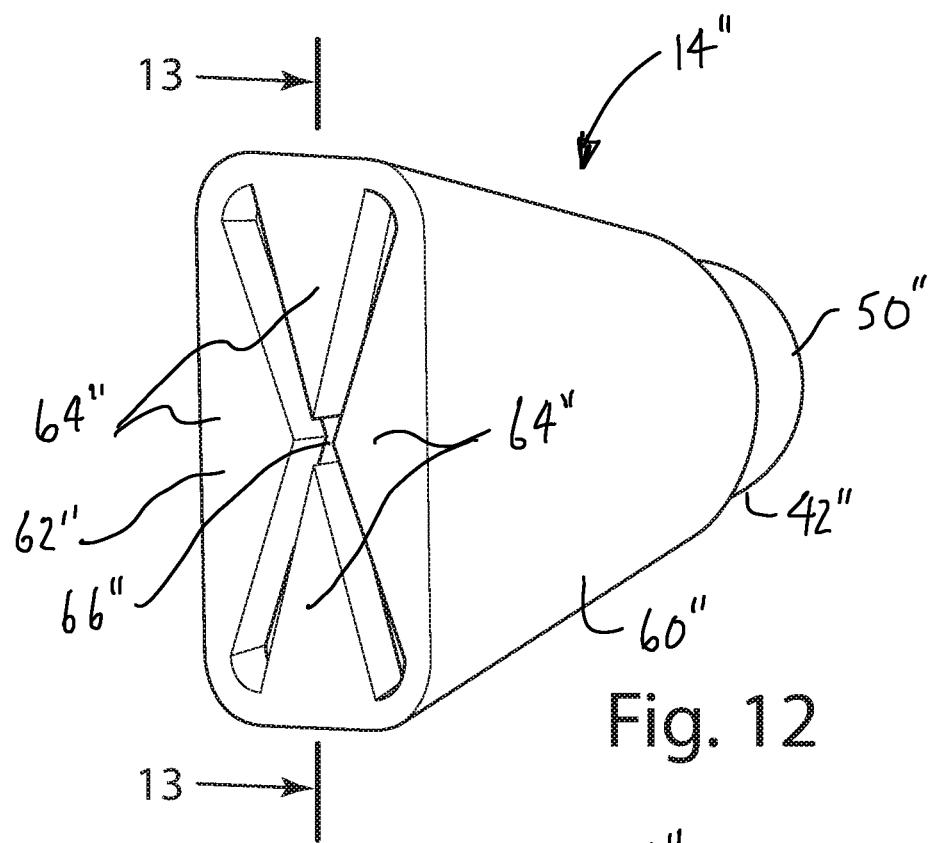
FIG. 12 is a perspective view of the third eyewear adaptor.
Figure 13:
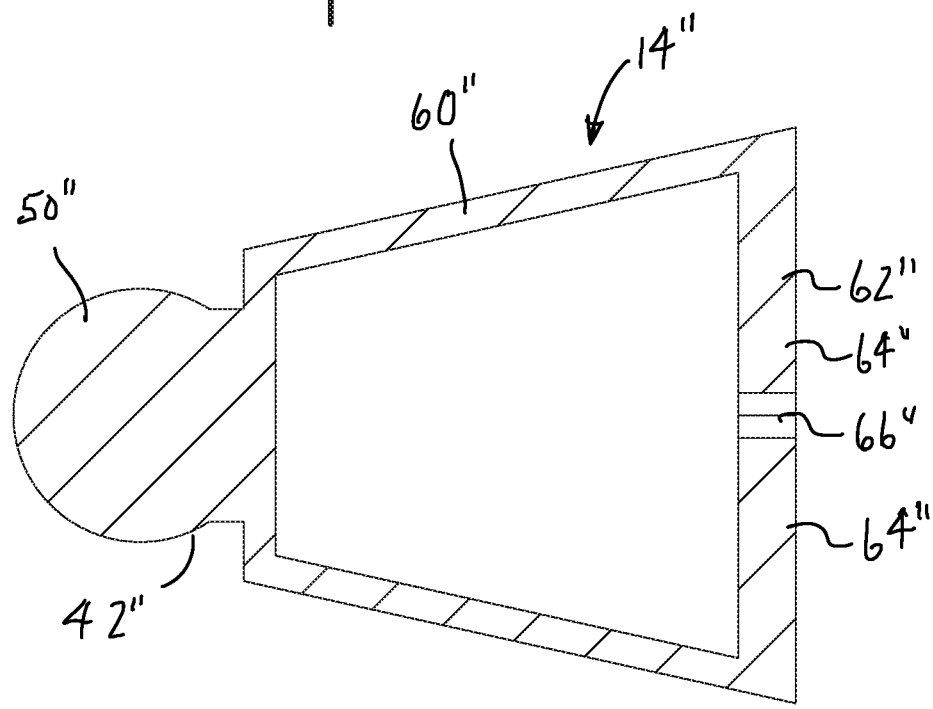
FIG. 13 is a sectional view of the third eyewear adaptor.

In the illustrated embodiment, the adaptor system 10 is provided as a kit with a plurality of alternative eyewear adaptors and/or a plurality of alternative audio processor adaptors that can be interchangeably used to join a wide range of cochlear audio processors to a wide range of eyewear. Although the illustrations show only a single audio processor adaptor 14, alternative audio processor adaptors with different audio processor interfaces or different attachment structures for connecting to different audio processors may be provided. Similarly, the adaptor system 10 may include a number of different eyewear adaptors each configured to attach to a particular size, type or style of temple or range of sizes, types or styles of temples. In the illustrated embodiment, the adaptor system 10 may be provided as a kit with three different eyewear adaptors 14, 14' and 14". FIGS. 10-13 show alternative eyewear adaptors 14' and 14". FIGS. 10-13 incorporate reference numerals that correspond with those used in connection with eyewear adaptor 14, except that elements of eyewear adaptor 14' are followed by a prime symbol " ' " and elements of eyewear adaptor 14" are followed by double prime symbol " " ". FIGS. 10 and 11 show a first alternative eyewear adaptor 14' in which the temple seat 60' and temple connector 62' are configured to receive a different of temples T than adaptor 14. As can be seen, the temple seat 60' of this embodiment is generally rectangular in shape and has the capability to receive large temples T than would fit in eyewear adaptor 14. As can be seen, the connector end 42' of this embodiment is essentially identical to connector end 42 so that it can interchangeably mount with essentially any audio processor adaptor and essentially any replacement temple tip. FIGS. 12 and 13 showing another alternative eyewear adaptor 14" with an even larger temple seat 60" and temple connector 62". In this embodiment, the temple seat 60" and temple connector 62" are configured to receive larger temple, such as the type commonly used with many plastic sunglass frames. As can be seen, the eyewear adaptors 14, 14', 14", audio processor adaptors 12 and replacement temple tips 80 and 90 are provided with universal connectors that allow any eyewear adaptor 14, 14' or 14" to be interchangeably connected to any audio processor adaptor 12 or to any replacement temple tip 80 or 90, thereby essentially allowing any eyewear to be easily joined to any audio processor or any replacement temple tip.

The audio processor adaptor 12 and the eyewear adaptor 14 may be manufactured using essentially any suitable methods and apparatus. For example, the audio processor adaptor 12 and/or the eyewear adaptor 14 may be molded, for example, injection molded using conventional injection molding equipment. As another example, the audio processor adaptor 12 and/or the eyewear adaptor 14 may be formed using 3D printing or other suitable additive manufacturing techniques. Although the illustrated adaptors 12 and 14 are each shown as one-piece constructions, they can alternatively be manufactured from multiple parts and/or using multiple materials. For example, the attachment end 20, connector end 22 and ear hook portion 24 of the audio processor adaptor 12 can be separately manufactured and joined, for example, by adhesives or press-fitted, in an assembly process. As another example, the eyewear adaptor 14 may be manufactured from two parts with the temple seat and connector end formed from as a first part and the temple connector formed as a second part. This approach may be used, for example, to allow the temple seat to be formed from a more rigid material suited for providing the adaptor 14 with sufficient structural rigidity and the temple connector to be formed from a more pliable and resilient material better suited for engaging with the temple.

In alternative embodiments, the adaptor system may include a replacement temple in addition or as an alternative to the eyewear adaptor. In such embodiments, the replacement temple includes a universal connector configured to removably receive either an audio processor adaptor or a replacement temple adaptor. For example, the free end of the replacement temple may be essentially identical to the connector end of the eyewear adaptor with a ball configured to be snap-fitted into the cup of the audio processor adaptor or the replacement temple tip. However, the replacement temple connector may vary from application to application in correspondence with the universal connector chosen for the adaptor system. The replacement temple may be configured to replace an existing temple in its entirety. More specifically, the replacement temple may include a mounting end that is configured to attach to the eyewear frames at the pre-existing attachment point for the stock temple. In use, the stock temple is removed from the frame attachment point by uninstalling the temple screw (e.g. at or near the temple hinge), and the replacement temple is attached to the frame attachment point by reinstalling the temple screw through the frame attachment point and the mounting end of the replacement temple. In some applications, the adaptor system may be provided with a plurality of different replacement temples that can be interchangeably installed to provide the best match or best fit with the eyewear frames.

The present invention is described in the context of a cochlear implant, and more specifically, to coupling an audio processor for a cochlear implant to an item of eyewear. The present invention may be adapted for use in attaching audio processors of other hearing-related devices, such as hearing aids, hearing protection devices and sound amplification devices.

The above description is that of current embodiments of the invention. Various alterations and changes can be made without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Any reference to claim elements in the singular, for example, using the articles "a," "an," "the" or "said," is not to be construed as limiting the element to the singular.

The embodiments of the invention in which an exclusive property or privilege is claimed are defined as follows:

1. An adaptor system for coupling an audio processor of a cochlear hearing implant to an item of eyewear comprising:
   an audio processor adaptor configured to mount to the audio processor, the audio processor adaptor having a first connector for connecting to the audio processor, an ear hook portion configured to engage a wearer's ear and a second connector; and
   an eyewear adaptor configured to mount to an item of eyewear, the eyewear adaptor having a first connector for connecting to a temple of the item of eyewear and a second connector removably connecting the eyewear adaptor to the audio processor adaptor;
   wherein the audio processor adaptor and the eyewear adaptor can be selectively joined to connect the audio processor to the item of eyewear and selectively separated to allow the audio processor with audio processor adaptor to be used in the absence of the item of eyewear;

wherein the first connector of the audio processor adaptor is configured to removably mount to an audio processor in place of a stock ear hook;

wherein the first connector of the audio processor adaptor and the second connector of the audio processor adaptor are disposed on opposite sides of the ear hook portion;

wherein the first connector of the eyewear adaptor includes a temple seat configured to receive a portion of a temple; and wherein the first connector of the eyewear adaptor includes a temple connector disposed over the mouth of the temple seat.

2. The adaptor system of claim 1 wherein the temple connector defines at least one temple receiving slot.

3. The adaptor system of claim 2 wherein the temple connector includes a plurality of resilient fingers defining the temple receiving slot.

4. The adaptor system of claim 3 wherein the second connector of the audio processor adaptor and the second connector of the eyewear adaptor include a ball and a cup, the ball and cup being selectively interfitable to selectively couple the audio processor adaptor to the eyewear adaptor.

5. The adaptor system of claim 4 wherein the eyewear adaptor includes the ball and the audio processor adaptor defines the cup.

6. The adaptor system of claim 5 further including a replacement temple tip having a temple portion and a connector configured to removably connect the temple tip replacement to the second connector of the eyewear adaptor when the audio processor adaptor is not connected the second connector of the eyewear adaptor.

7. An adaptor system kit comprising:
an audio processor adaptor configured to mount to an audio processor for a cochlear implant wherein the audio processor has a removable ear hook, the audio processor adaptor having a first connector configured to attach to the audio processor in place of the removable ear hook, the audio processor adaptor having an ear hook portion configured to fit with a wearer's ear, the audio processor adaptor having a second connector;
a plurality of eyewear adaptors configured to interchangeably connect to the audio processor adaptor, each eyewear adaptor having a temple connector configured to connect to a range of different eyewear temples, each temple connector being different from the temple connectors of the other eyewear adaptors, each eyewear adaptor having a third connector configured to removably couple to the second connector of the audio processor adaptor; and
wherein the audio processor adaptor and one of the plurality of eyewear adaptors can be selectively joined to couple the audio processor to an item of eyewear, thereby facilitating the simultaneous use of the eyewear and the audio processor;
wherein the audio processor adaptor can be selectively separated from the eyewear adaptors while remaining connected to the audio processor, thereby facilitating use of the audio processor separate from the eyewear.

8. The adaptor system kit of claim 7 further including a replacement temple tip configured to selectively and interchangeably mount to each of the eyewear adaptors, the replacement temple tip having a temple tip portion in the form of a temple tip shaped to engage a wearer's ear, the replacement temple tip having a fourth connector configured to removably connect to the third connector of the eyewear adaptor, whereby attachment of the replacement temple tip to the eyewear adaptor provides the temple to which the eyewear adaptor is mounted with a temple tip, thereby facilitating use of the eyewear separate from the audio processor.

9. The adaptor system kit of claim 7 wherein the temple connector of each eyewear adaptor includes a temple seat configured to receive a portion of a temple.

10. The adaptor system kit of claim 9 wherein the temple connector of the eyewear adaptor includes a temple connector disposed over the mouth of the temple seat.

11. The adaptor system kit of claim 10 wherein the temple connector includes a plurality of resilient fingers defining a temple receiving slot.

12. The adaptor system kit of claim 7 wherein the first connector of the audio processor adaptor and the second connector of the audio processor adaptor are disposed on opposite sides of the ear hook portion.

13. The adaptor system kit of claim 7 wherein the second connector of the audio processor adaptor and the second connector of the eyewear adaptor are selectively connectable by a snap-fit connection.

14. The adaptor system kit of claim 7 wherein the second connector of the audio processor adaptor and the second connector of the eyewear adaptor include a ball and a cup, the ball and cup being selectively interfitable to selectively couple the audio processor adaptor to the eyewear adaptor.

15. The adaptor system kit of claim 13 wherein the eyewear adaptor includes the ball and the audio processor adaptor defines the cup.

16. A method of use of an adaptor system for an audio processor and an item of eyewear, comprising the steps of:
attaching an audio processor adaptor to an audio processor, the audio processor adaptor having an ear hook portion and being mounted to the audio processor in place of a stock ear hook;
attaching an eyewear adaptor to an item of eyewear, the eyewear adaptor being attached to the temple of the eyewear after removing a portion of the temple;
selectively connecting the audio processor adaptor to the eyewear adaptor to couple the eyewear to the audio processor, whereby the eyewear and the audio processor may be worn together by a user;
selectively removing the audio processor adaptor from the eyewear adaptor, whereby the audio processor may be worn over an ear separate from the eyewear; and
selectively connecting a replacement temple tip to the eyewear adaptor, whereby the eyewear can be worn separate from the audio processor.

* * * * *